(12) United States Patent
Yoshino

(10) Patent No.: US 10,574,874 B2
(45) Date of Patent: Feb. 25, 2020

(54) ENDOSCOPE APPARATUS, METHOD FOR CONTROLLING ENDOSCOPE APPARATUS, AND INFORMATION STORAGE DEVICE

(71) Applicant: OLYMPUS CORPORATION, Hachioji-shi, Tokyo (JP)

(72) Inventor: Koichiro Yoshino, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 445 days.

(21) Appl. No.: 15/099,377

(22) Filed: Apr. 14, 2016

(65) Prior Publication Data
US 2016/0234427 A1 Aug. 11, 2016

Related U.S. Application Data

(63) Continuation of application No. PCT/JP2014/075620, filed on Sep. 26, 2014.

(30) Foreign Application Priority Data

Dec. 27, 2013 (JP) .................................. 2013-271151

(51) Int. Cl.
*H04N 5/232* (2006.01)
*G02B 23/24* (2006.01)
(Continued)

(52) U.S. Cl.
CPC ..... *H04N 5/23212* (2013.01); *A61B 1/00006* (2013.01); *A61B 1/00009* (2013.01);
(Continued)

(58) Field of Classification Search
None
See application file for complete search history.

(56) References Cited

U.S. PATENT DOCUMENTS 7,463,302 B2 12/2008 Kobayashi
8,717,490 B2 5/2014 Imamura et al.
(Continued)

FOREIGN PATENT DOCUMENTS

CN 101931752 A 12/2010
JP 09253041 A 9/1997
(Continued)

OTHER PUBLICATIONS

Extended European Search Report (EESR) dated Oct. 2, 2017 issued in couterpart European Application No. 14874528.4.
(Continued)

*Primary Examiner* — Dakshesh D Parikh
(74) *Attorney, Agent, or Firm* — Holtz, Holtz & Volek PC

(57) ABSTRACT

An endoscope apparatus includes a processor comprising hardware, a processor performs a focus control that controls a position of a focus lens to an in-focus position based on an in-focus evaluation value, the focus lens being included in an optical system that forms an image of a captured image that is acquired by an imaging section, and the in-focus evaluation value being calculated from a first area within the captured image, and a change-in-scene detection process that detects whether or not a change in scene has occurred from a second area that includes an area that differs from the first area, wherein the processor is set to a standby state when the position of the focus lens has been controlled to the in-focus position, and resumes the focus control process when a change in scene has been detected when the focus control section is set to the standby state.

14 Claims, 10 Drawing Sheets

IMAGE WHILE USER PERFORMS TREATMENT

(51) Int. Cl.
*H04N 9/04* (2006.01)
*A61B 1/00* (2006.01)
*A61B 1/04* (2006.01)
*A61B 1/045* (2006.01)
*G02B 7/09* (2006.01)
*H04N 5/14* (2006.01)
*H04N 5/225* (2006.01)

(52) U.S. Cl.
CPC ...... *A61B 1/00036* (2013.01); *A61B 1/00188* (2013.01); *A61B 1/042* (2013.01); *A61B 1/045* (2013.01); *G02B 7/09* (2013.01); *G02B 23/2438* (2013.01); *G02B 23/2476* (2013.01); *G02B 23/2484* (2013.01); *H04N 5/147* (2013.01); *H04N 5/23296* (2013.01); *H04N 9/045* (2013.01); *H04N 2005/2255* (2013.01)

(56) References Cited

U.S. PATENT DOCUMENTS

| | | | |
|---|---|---|---|
| 2004/0130651 | A1 | 7/2004 | Wakashiro |
| 2009/0010551 | A1* | 1/2009 | Matsuda ............... A61B 1/041 382/228 |
| 2009/0046196 | A1 | 2/2009 | Lavrentiev et al. |
| 2009/0273704 | A1* | 11/2009 | Pincenti ............ H04N 5/23212 348/349 |
| 2010/0283842 | A1* | 11/2010 | Guissin ................. G02B 13/06 348/68 |
| 2012/0147165 | A1* | 6/2012 | Yoshino ............. H04N 5/23212 348/65 |
| 2013/0188029 | A1* | 7/2013 | Takahashi .......... H04N 5/23212 348/65 |
| 2014/0111628 | A1 | 4/2014 | Yoshino et al. |
| 2014/0300716 | A1* | 10/2014 | Tsuruoka .......... G02B 23/2484 348/65 |

FOREIGN PATENT DOCUMENTS

| | | | | |
|---|---|---|---|---|
| JP | 2002253488 | A | 9/2002 | |
| JP | 2004205982 | A | 7/2004 | |
| JP | 2006208818 | A | 8/2006 | |
| JP | 2009058932 | A | 3/2009 | |
| JP | 2010176061 | A | 8/2010 | |
| JP | 2011090048 | A | 5/2011 | |
| JP | 2013043007 | A | 3/2013 | |
| JP | 2013061618 | A | 4/2013 | |
| JP | WO 2013108580 | A1 * | 7/2013 | ............ G03B 13/36 |
| JP | 2013146289 | A | 8/2013 | |
| JP | 2013230289 | A | 11/2013 | |

OTHER PUBLICATIONS

International Search Report (ISR) dated Jan. 6, 2015 issued in International Application No. PCT/JP2014/075620.

* cited by examiner

CHANGE-IN-SCENE DETECTION AREA AND AF AREA

IMAGE WHILE USER PERFORMS TREATMENT

CHANGE-IN-SCENE DETECTION AREA AND AF AREA

MOTION VECTOR WHEN RIGID SCOPE HAS BEEN MOVED IN LEFTWARD DIRECTION

MOTION VECTOR WHEN RIGID SCOPE HAS BEEN MOVED CLOSER TO OBJECT

MOTION VECTOR WHEN RIGID SCOPE HAS BEEN MOVED AWAY FROM OBJECT

EFFECTIVE BLOCK DETERMINATION FLAG SET TO FIRST IMAGE

EFFECTIVE BLOCK DETERMINATION FLAG SET TO SECOND IMAGE

EFFECTIVE BLOCK DETERMINATION FLAG USED TO CALCULATE IN-FOCUS EVALUATION VALUE

ENDOSCOPE APPARATUS, METHOD FOR CONTROLLING ENDOSCOPE APPARATUS, AND INFORMATION STORAGE DEVICE

CROSS REFERENCE TO RELATED APPLICATION

This application is a continuation of International Patent Application No. PCT/JP2014/075620, having an international filing date of Sep. 26, 2014, which designated the United States, the entirety of which is incorporated herein by reference. Japanese Patent Application No. 2013-271151 filed on Dec. 27, 2013 is also incorporated herein by reference in its entirety.

BACKGROUND

The present invention relates to an endoscope apparatus, a method for controlling an endoscope apparatus and an information storage device.

A depth of field as deep as possible is required for an endoscope apparatus (endoscope system) so that the user can easily perform diagnosis and treatment. In recent years, an image sensor having a large number of pixels has been used for the endoscope system, and the depth of field of the endoscope system has become shallow. Therefore, an endoscope system that performs an autofocus (AF) process has been proposed. The following techniques have been proposed to prevent a situation in which the focus operation is unnecessarily performed when capturing a video (moving image).

JP-A-2006-208818 discloses a technique that stores the AF evaluation value (in-focus evaluation value) acquired when the focus operation has been completed, and performs the focus operation again when a change in the AF evaluation value that is equal to or larger than a given threshold value has continuously occurred for a time equal to or longer than a given standby time. This technique makes it possible to suppress a situation in which the focus operation is unnecessarily performed (i.e., the focus operation is performed too frequently).

JP-A-2010-176061 discloses a technique that sets the AF area in the center area of the image, and calculates the degree of similarity in the peripheral area between the current image and the previous image, and the degree of similarity in the center area (AF area) between the current image and the previous image. Note that the degree of similarity used in JP-A-2010-176061 decreases as the comparison target images are more similar to each other. According to the technique disclosed in JP-A-2010-176061, the focus operation is not performed when the degree of similarity in the peripheral area is equal to or larger than a given threshold value, and the degree of similarity in the center area is equal to or smaller than a given threshold value. According to the technique disclosed in JP-A-2010-176061, it is possible to suppress a situation in which the focus operation is unnecessarily performed even if the object captured within the peripheral area of the image has changed due to a change in framing or the like, as long as the distance to the main object situated in the center area of the image does not change.

The user of an endoscope system (particularly a surgical endoscope system) operates the endoscope so that a lesion is situated around the center of the image, and performs treatment (e.g., excision of a lesion or suture) using a treatment tool (e.g., electrosurgical knife or forceps). Therefore, it is desirable that the endoscope system be configured so that the AF area is situated around the center of the image.

It is desirable to stop the focus operation after the user has fixed the field of view in order to perform treatment, and the focus operation controlled by the AF control process has been completed, in order to suppress or reduce the occurrence of defocus or the like due to an unintentional change in focus position or erroneous AF control.

Since the user performs treatment (e.g., excision or suture) on a lesion that is situated around the center of the image, a large motion of the treatment tool, or a change in position or shape of the lesion occurs around the center of the image during treatment. As a result, a similar image is not obtained in the center area (AF area) of the image, and the AF evaluation value changes to a large extent when the user performs treatment.

SUMMARY

According to one aspect of the invention, there is provided an endoscope apparatus comprising:

a processor comprising hardware, the processor being configured to implement:

a focus control process that controls a position of a focus lens to an in-focus position based on an in-focus evaluation value, the focus lens being included in an optical system that forms an image included in a captured image that is acquired by an imaging section, and the in-focus evaluation value being calculated from a first area within the captured image; and a change-in-scene detection process that detects whether or not a change in scene has occurred from a second area within the captured image that includes an area that differs from at least the first area, wherein the processor is set to a standby state in which the processor stops the focus control process when the focus control process has controlled the position of the focus lens to the in-focus position, and resumes the focus control process when the change in scene has been detected by the change-in-scene detection process when the processor is set to the standby state.

According to another aspect of the invention, there is provided a method for controlling an endoscope apparatus comprising:

calculating an in-focus evaluation value from a first area within a captured image from an imaging section;

performing a focus control process that controls a position of a focus lens to an in-focus position based on the in-focus evaluation value, the focus lens being included in an optical system included in the imaging section;

detecting whether or not a change in scene has occurred from a second area within the captured image that includes an area that differs from at least the first area; and resuming the focus control process when the change in scene has been detected in a standby state in which the focus control process is stopped after the focus control process has controlled the position of the focus lens to the in-focus position.

According to another aspect of the invention, there is provided a computer-readable storage device with an executable program stored thereon, wherein the program instructs a microprocessor to perform the following steps of;

calculating an in-focus evaluation value from a first area within a captured image from an imaging section;

performing a focus control process that controls a position of a focus lens to an in-focus position based on the in-focus evaluation value, the focus lens being included in an optical system included in the imaging section;

detecting whether or not a change in scene has occurred from a second area within the captured image that includes an area that differs from at least the first area; and resuming the focus control process when the change in scene has been detected in a standby state in which the focus control process is stopped after the focus control process has controlled the position of the focus lens to the in-focus position.

DESCRIPTION OF EXEMPLARY EMBODIMENTS

Figure 1:
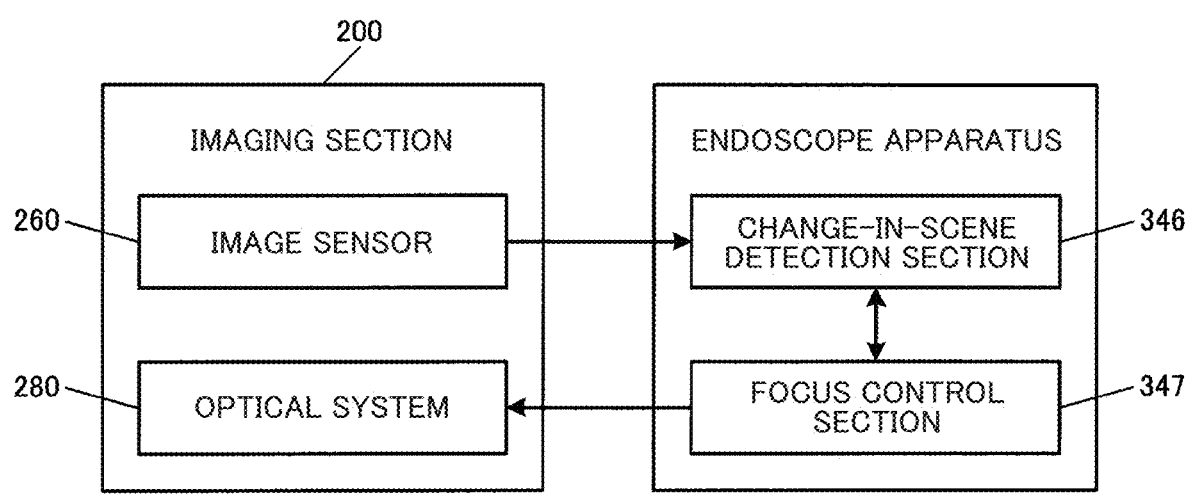
FIG. 1 illustrates a configuration example of an endoscope apparatus according to one embodiment of the invention.

According to one embodiment of the invention, there is provided an endoscope apparatus comprising:

a processor comprising hardware, the processor being configured to implement:

a focus control process that controls a position of a focus lens to an in-focus position based on an in-focus evaluation value, the focus lens being included in an optical system that forms an image included in a captured image that is acquired by an imaging section, and the in-focus evaluation value being calculated from a first area within the captured image; and a change-in-scene detection process that detects whether or not a change in scene has occurred from a second area within the captured image that includes an area that differs from at least the first area, wherein the processor is set to a standby state in which the processor stops the focus control process when the focus control process has controlled the position of the focus lens to the in-focus position, and resumes the focus control process when the change in scene has been detected by the change-in-scene detection process when the processor is set to the standby state.

According to another embodiment of the invention, there is provided a method for controlling an endoscope apparatus comprising:

calculating an in-focus evaluation value from a first area within a captured image from an imaging section;

performing a focus control process that controls a position of a focus lens to an in-focus position based on the in-focus evaluation value, the focus lens being included in an optical system included in the imaging section;

detecting whether or not a change in scene has occurred from a second area within the captured image that includes an area that differs from at least the first area; and resuming the focus control process when the change in scene has been detected in a standby state in which the focus control process is stopped after the focus control process has controlled the position of the focus lens to the in-focus position.

According to another embodiment of the invention, there is provided an information storage device storing a program that causes a computer to perform steps of:

calculating an in-focus evaluation value from a first area within a captured image from an imaging section;

performing a focus control process that controls a position of a focus lens to an in-focus position based on the in-focus evaluation value, the focus lens being included in an optical system included in the imaging section;

detecting whether or not a change in scene has occurred from a second area within the captured image that includes an area that differs from at least the first area; and resuming the focus control process when the change in scene has been detected in a standby state in which the focus control process is stopped after the focus control process has controlled the position of the focus lens to the in-focus position.

Exemplary embodiments of the invention are described below. Note that the following exemplary embodiments do not in any way limit the scope of the invention laid out in the claims. Note also that all of the elements described below in connection with the following exemplary embodiments should not necessarily be taken as essential elements of the invention.

1. Method

As described above, an image sensor having a large number of pixels has been used for an endoscope apparatus, and the depth of field of the endoscope apparatus has become shallow. Therefore, an endoscope apparatus that performs an AF process (operation) has been proposed. However, since the AF process searches (finds) the position of the focus lens at which the in-focus state is achieved while adjusting the position of the focus lens, the position of the focus lens is changed during the AF process. Specifically, since the AF process searches (finds) the peak of the in-focus evaluation value (AF evaluation value) while moving the position of the focus lens in a given direction, the focus position may change during the focus operation, whereby defocus or the like may occur. When the user has pulled a non-treatment target part of tissue forward in order to facilitate treatment, for example, the position of the focus lens may be changed so that the non-treatment target part is brought into focus, and the treatment target part may become out of focus.

Specifically, the focus operation may hinder observation, diagnosis, treatment, or the like performed by the user when the focus operation is performed in a situation in which the user considers that the AF operation (focus operation) is unnecessary. According to the technique disclosed in JP-A-2006-208818 or JP-A-2010-176061, a device that performs the AF process (operation) is controlled so that the focus operation is stopped, or the focus operation that has been stopped (standby state) is not resumed corresponding to the situation.

Figure 5A:
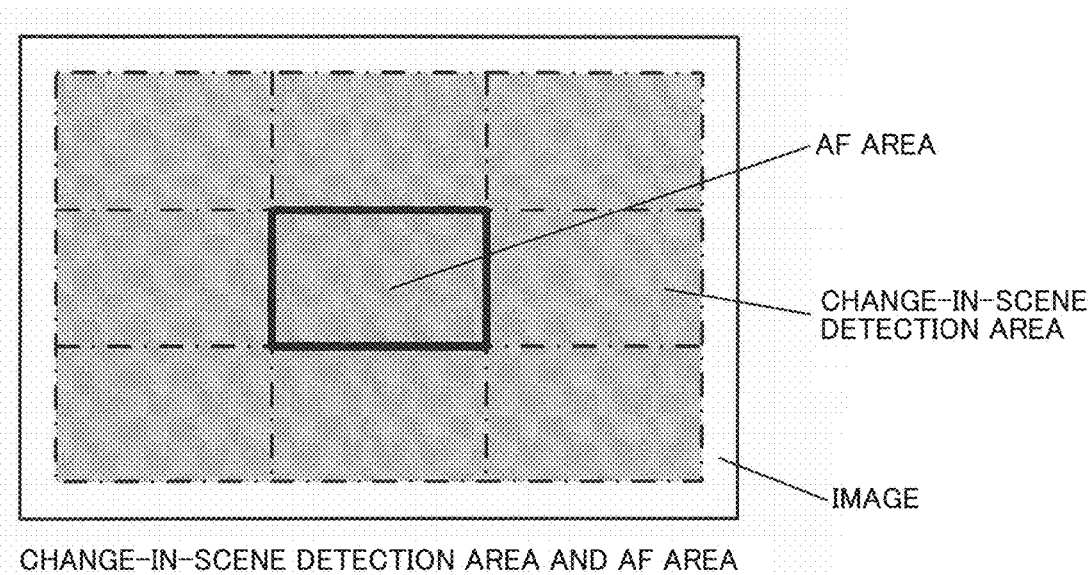
FIG. 5A illustrates a first area/second area setting example.
Figure 5B:
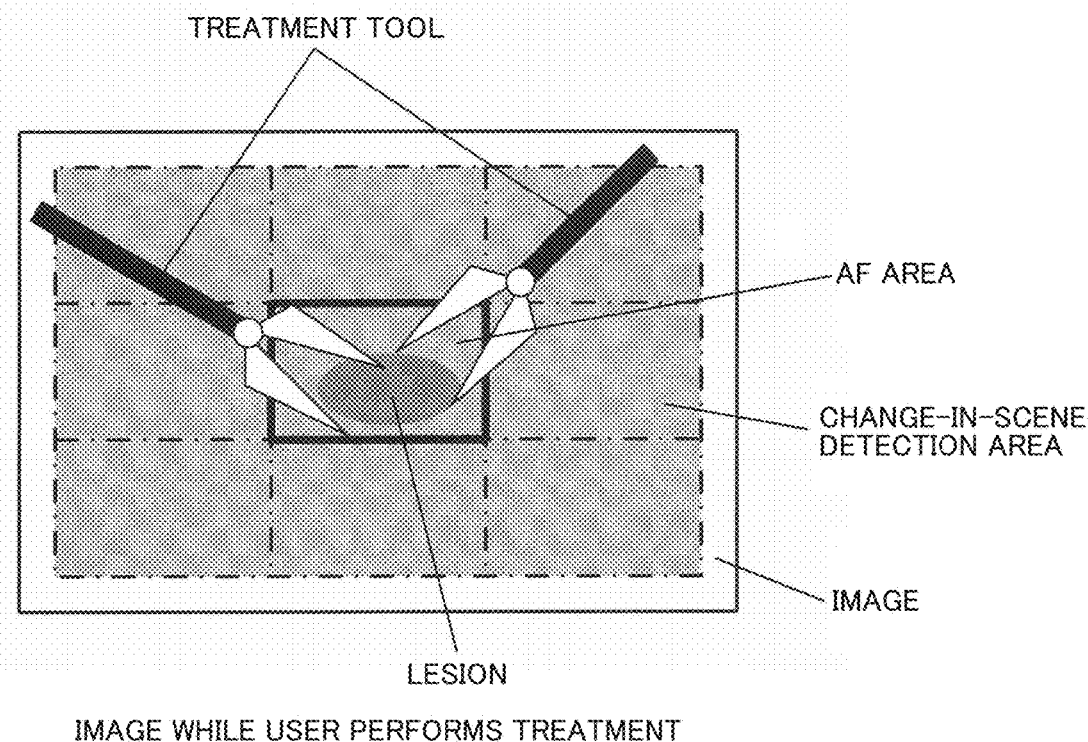
FIG. 5B illustrates a situation during treatment, and the relationship between the first area and the second area.

Several embodiments of the invention may be applied to a situation in which treatment is performed on tissue using a treatment tool (e.g., forceps) provided to the end of an insertion section (imaging section 200) of an endoscope apparatus (see FIG. 5B). In this case, it is considered that the object (treatment target) has been brought into focus when the user starts treatment since it is difficult to appropriately perform treatment in a state in which the object is out of focus. It is considered that the user (doctor) normally does not perform an operation that changes the in-focus state to a large extent (e.g., an operation that moves the imaging section to a large extent) prior to completion of treatment. Specifically, it is likely that the focus operation is unnecessary (i.e., it is unnecessary to cancel the AF standby state) when the user performs treatment (see FIG. 5B), and it is desirable to stop the focus operation (continue the standby state) when the user performs treatment from the viewpoint of suppressing or reducing the adverse effect (e.g., defocus) due to the focus operation.

However, since the user performs treatment (e.g., excision or suture) on a lesion that is situated around the center of the image, a large motion of the treatment tool, or a change in position or shape of the lesion occurs around the center of the image during treatment. Therefore, it is difficult to stop the focus operation during treatment using the technique disclosed in JP-A-2006-208818 or JP-A-2010-176061.

In particular, since the object that is brought into focus using the AF process (hereinafter may be referred to as "main object") is the treatment target object, the treatment target object has a significantly high degree of contribution to the in-focus evaluation value. Specifically, it is likely that the in-focus evaluation value changes to a large extent, and the focus operation is unnecessary when the user performs treatment (see FIG. 5B). According to the technique disclosed in JP-A-2006-208818, however, the focus operation is performed even in such a situation.

According to the technique disclosed in JP-A-2010-176061, the focus operation is not performed when the degree of similarity in the center area of the image is high independently of the degree of similarity in the peripheral area of the image (e.g., even when the degree of similarity in the peripheral area is low). The technique disclosed in JP-A-2010-176061 is designed on the assumption that the main object is captured in the center area, and the focus operation is not performed on condition that a change in main object does not occur. However, since a change in main object occurs to a large extent during treatment as compared with the remaining area, the focus operation is performed in a situation in which the focus operation is unnecessary when using the technique disclosed in JP-A-2010-176061.

In order to solve the above problems, several embodiments of the invention propose a method that detects a change in scene from an area that includes an area that differs from the main object. The relationship between the in-focus evaluation value calculation target area and the change-in-scene detection target area is appropriately set taking account of the fact that the main object is the object that is brought into focus using the AF process. According to several embodiments of the invention, an endoscope apparatus includes a focus control section 347 that performs a focus control process that controls the position of a focus lens (focus lens 220 illustrated in FIG. 2) to an in-focus position based on an in-focus evaluation value, the focus lens being included in an optical system 280 (corresponding to an objective lens system 270 illustrated in FIG. 2) that forms an image of a captured image that is acquired by an imaging section 200, and the in-focus evaluation value being calculated from a first area within the captured image, and a change-in-scene detection section 346 that detects whether or not a change in scene has occurred from a second area within the captured image that includes an area that differs from at least the first area (see FIG. 1). The focus control section 347 is set to a standby state in which the focus control section 347 stops the focus control process when the focus control process has controlled the position of the focus lens to the in-focus position, and resumes the focus control process when the change-in-scene detection section 346 has detected a change in scene when the focus control section 347 is set to the standby state.

The term "change in scene" used herein refers to a case where the object that is captured has changed, and a case where the object that is captured is the same, but the distance from the imaging section, the direction from the imaging section, or the like has changed to a large extent, for example. Specifically, it is considered that the focus operation must be performed again when a change in scene has been detected. Note that the details of the change-in-scene detection method are described later. The captured image from the imaging section 200 may be an output image that is output from an image sensor, or may be an image obtained by extracting an arbitrary area from the output image. For example, when the image circle is small, and the output image includes an area in which an object image is formed (hereinafter referred to as "object-captured area"), and an area in which an object image is not formed (see the second embodiment), the captured image may be an object-captured image that corresponds to the object-captured area.

The term "focus control process" used herein refers to a control process that searches (finds) the position (in-focus position or in-focus lens position) of the focus lens at which the object is brought into focus using the in-focus evaluation value. More specifically, the steps S101 to S104 illustrated in FIG. 4 (flowchart) correspond to the focus control process. Note that the term "focus control process" used herein in a broad sense includes a control process that sets (controls) the focus lens to the in-focus position (i.e., a control process that controls the focus operation), a control process that stops the focus operation, a control process that resumes the focus operation that has been stopped, and the like. More specifically, the focus control process in a broad sense corresponds to the entire flowchart illustrated in FIG. 4 that includes the focus operation (S101 to S104) and the standby operation (S201 and S202).

According to this configuration, it is possible to detect a change in scene using the second area that includes an area that differs from the first area. The first area is the in-focus evaluation value calculation target area, and corresponds to the treatment target object during treatment. Therefore, the object captured in the first area changes to a large extent due to treatment, and the object captured in an area that differs from the first area changes to only a small extent (makes only a small motion). Specifically, when the second area that includes an area that differs from at least the first area, it is determined that a change in scene has not occurred even when the treatment target object has changed. This makes it possible to suppress a situation in which the focus operation is unnecessarily performed.

When the object that is captured changes to a large extent, a large change also occurs in an area that differs from the first area. Therefore, the focus operation is necessarily performed when the focus operation is necessary.

Although an example in which the endoscope apparatus according to several embodiments of the invention cancels the standby state, and resumes the focus operation when a change in scene has been detected has been described above, the focus operation need not necessarily be resumed only when a change in scene has been detected. Specifically, the detection of a change in scene is one of the conditions whereby the focus operation is resumed, and the focus operation may be resumed based on another condition. The term "change in scene" may include a timing at which a change in scene has been detected (i.e., a timing at which a change in scene has started), and a timing at which a change in scene stops.

In FIG. 1, the imaging section 200 is illustrated outside the endoscope apparatus. When performing treatment using an endoscope apparatus, a rigid scope (rigid scope 100) may normally be exchanged corresponding to treatment, and the imaging section 200 may also be exchanged. In such a case, the device that performs the change-in-scene detection process and the like, and the imaging section 200 may be produced and sold separately. Therefore, the endoscope apparatus according to several embodiments of the invention need not necessarily include the imaging section 200. Note that the endoscope apparatus according to several embodiments of the invention may include the imaging section 200 (as described later with reference to FIG. 2).

The first to third embodiments of the invention are described below. The first embodiment illustrates a basic method, the second embodiment illustrates a method that takes account of the image circle diameter, and the third embodiment illustrates a method that takes account of whether each block included in the second area is effective or ineffective.

2. First Embodiment

Figure 2:
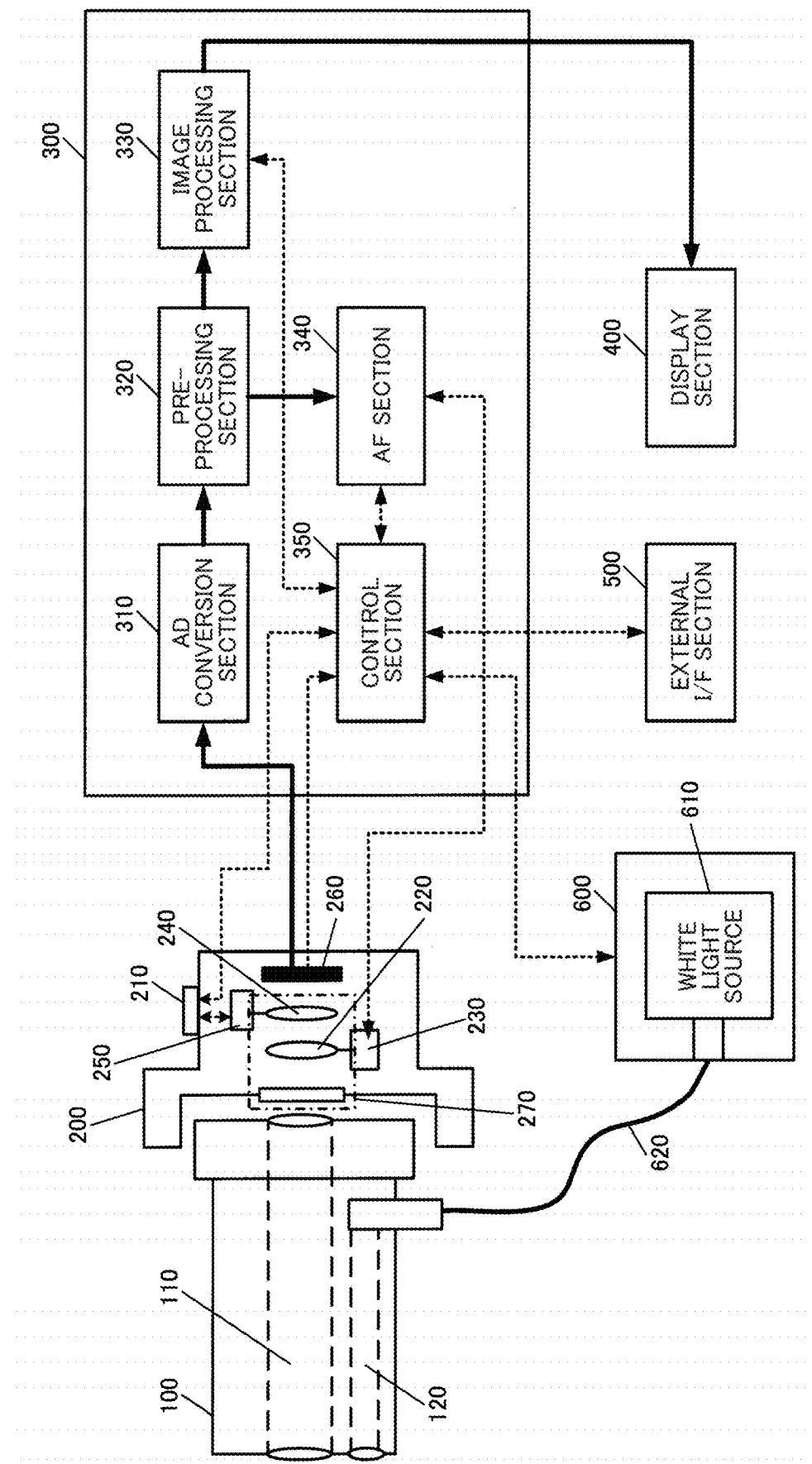
FIG. 2 illustrates a detailed system configuration example of an endoscope apparatus according to one embodiment of the invention.

An endoscope system according to the first embodiment is described below with reference to FIG. 2. The endoscope system according to the first embodiment includes a rigid scope 100 (i.e., an insertion section that is inserted into a body), an imaging section 200 that is connected to the rigid scope 100, a processing section 300, a display section 400, an external I/F section 500, and a light source section 600.

The light source section 600 includes a white light source 610 that emits white light, and a light guide cable 620 that guides the light emitted from the white light source 610 to the rigid scope 100.

The rigid scope 100 includes a lens system 110 that includes an imaging lens, a relay lens, an eyepiece, and the like, and a light guide section 120 that guides the light that has passed through the light guide cable 620 to the end of the rigid scope 100.

The imaging section 200 includes an objective lens system 270 that forms an image from the light that has passed through the lens system 110. The objective lens system 270 includes a focus lens 220 that adjusts the in-focus object plane position, and a zoom lens 240 that adjusts the optical magnification. The imaging section 200 further includes an image sensor 260 that photoelectrically converts the reflected light that has passed through the objective lens system 270 to generate an image, a focus lens driver section 230 that drives the focus lens 220, a zoom lens driver section 250 that drives the zoom lens 240, and a zoom button 210 that is used to adjust the position of the zoom lens. The focus lens driver section 230 and the zoom lens driver section 250 are implemented by a voice coil motor (VCM), for example.

The image sensor 260 is a solid-state image sensor that includes a Bayer color filter array, for example.

The processing section 300 includes an AD conversion section 310, a pre-processing section 320, an image processing section 330, an AF section 340, and a control section 350. The AD conversion section 310 converts analog signals sequentially output from the image sensor 260 into a digital image, and sequentially outputs the digital image to the pre-processing section 320. The pre-processing section 320 performs image processing (e.g., white balance process, interpolation process (demosaicing process), and YCbCr conversion process) on the image output from the AD conversion section 310, and sequentially outputs the resulting image to the image processing section 330 and the AF section 340. The details of the AF section 340 are described later.

The image processing section 330 performs image processing (e.g., color conversion process, grayscale transformation process, edge enhancement process, and noise reduction process) on the image output from the pre-processing section 320, and sequentially outputs the resulting image to the display section 400. The display section 400 is a liquid crystal monitor, for example. The display section 400 displays the image sequentially output from the image processing section 330.

The control section 350 is bidirectionally connected to the external I/F section 500, the image processing section 330, the AF section 340, the image sensor 260, the zoom button 210, and the like, and exchanges a control signal with the external I/F section 500, the image processing section 330, the AF section 340, the image sensor 260, the zoom button 210, and the like. The external I/F section 500 is an interface that allows the user to perform an input operation or the like on the endoscope apparatus. The external I/F section 500 includes an AF button (AF start/stop button), an adjustment button (image processing parameter adjustment button), and the like.

Figure 3:
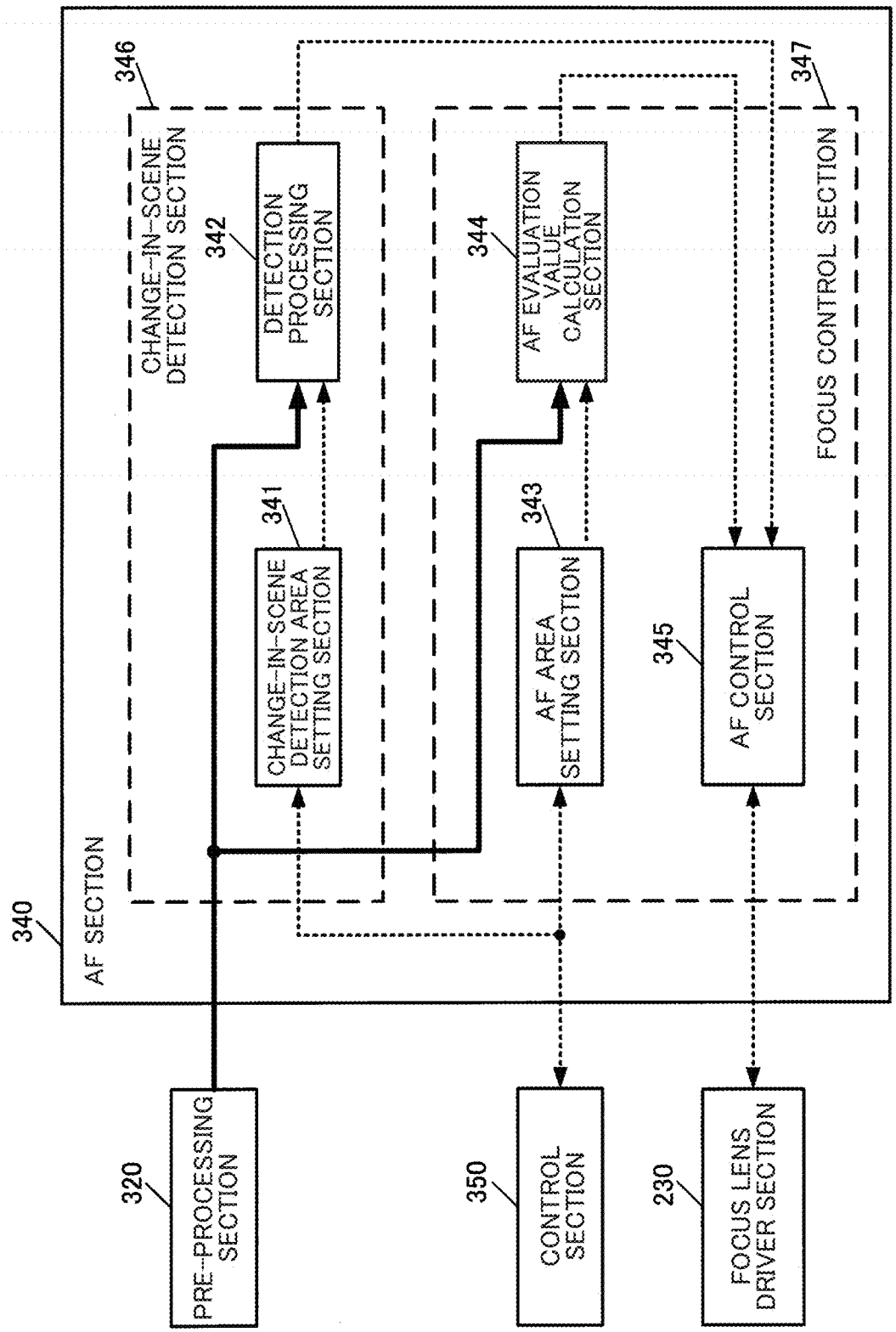
FIG. 3 illustrates a configuration example of an AF section.

The details of the AF section 340 are described below with reference to FIG. 3. The AF section 340 includes a change-in-scene detection section 346 and a focus control section 347. The change-in-scene detection section 346 includes a change-in-scene detection area setting section 341 and a detection processing section 342, and the focus control section 347 includes an AF area setting section 343, an AF evaluation value calculation section 344, and an AF control section 345.

The change-in-scene detection area setting section 341 sets a change-in-scene detection area (corresponding to the second area) as illustrated in FIG. 5A based on information (e.g., image size) output from the control section 350, for example. The change-in-scene detection area setting section 341 outputs change-in-scene detection area information about the change-in-scene detection area set by the change-in-scene detection area setting section 341 to the detection processing section 342. In the first embodiment, nine evaluation blocks are set to the image, and a set of these evaluation blocks is set to be the change-in-scene detection area. Note that the number of evaluation blocks set to be the change-in-scene detection area can be set arbitrarily.

The detection processing section 342 detects a change in scene based on the change-in-scene detection area information output from the change-in-scene detection area setting section 341, and the image sequentially output from the pre-processing section 320. The detection processing section 342 outputs change-in-scene detection information that represents whether or not a change in scene has been detected to the AF control section 345. The details of the change-in-scene detection method are described later.

The AF area setting section 343 sets an AF area (corresponding to the first area) as illustrated in FIG. 5A based on information (e.g., image size) output from the control section 350, for example. The AF area setting section 343 outputs AF area information about the AF area set by the AF area setting section 343 to the AF evaluation value calculation section 344. In the first embodiment, an area that is identical to the evaluation block that is included in a plurality of evaluation blocks set to be the change-in-scene detection area and is situated at the center is set to be the AF area for convenience of explanation. Since the evaluation block and the AF area need not necessarily have an identical size, an area that differs in size from the evaluation block may be set around (in the vicinity of) the center of the image as the AF area.

The AF evaluation value calculation section 344 sequentially calculates an AF evaluation value based on the AF area information output from the AF area setting section 343 and the image sequentially output from the pre-processing section 320. For example, a band-pass filtering (BPF) process is performed on the Y signal of each pixel included in the AF area, and the sum of the output values is used as the AF evaluation value. The AF evaluation value calculation section 344 sequentially outputs the calculated AF evaluation value to the AF control section 345.

The AF control section 345 performs an AF process by controlling the focus lens based on the change-in-scene detection information output from the detection processing section 342 and the AF evaluation value output from the AF evaluation value calculation section 344. The focus lens driver section 230 drives the focus lens based on a focus lens control signal output from the AF control section 345.

Figure 4:
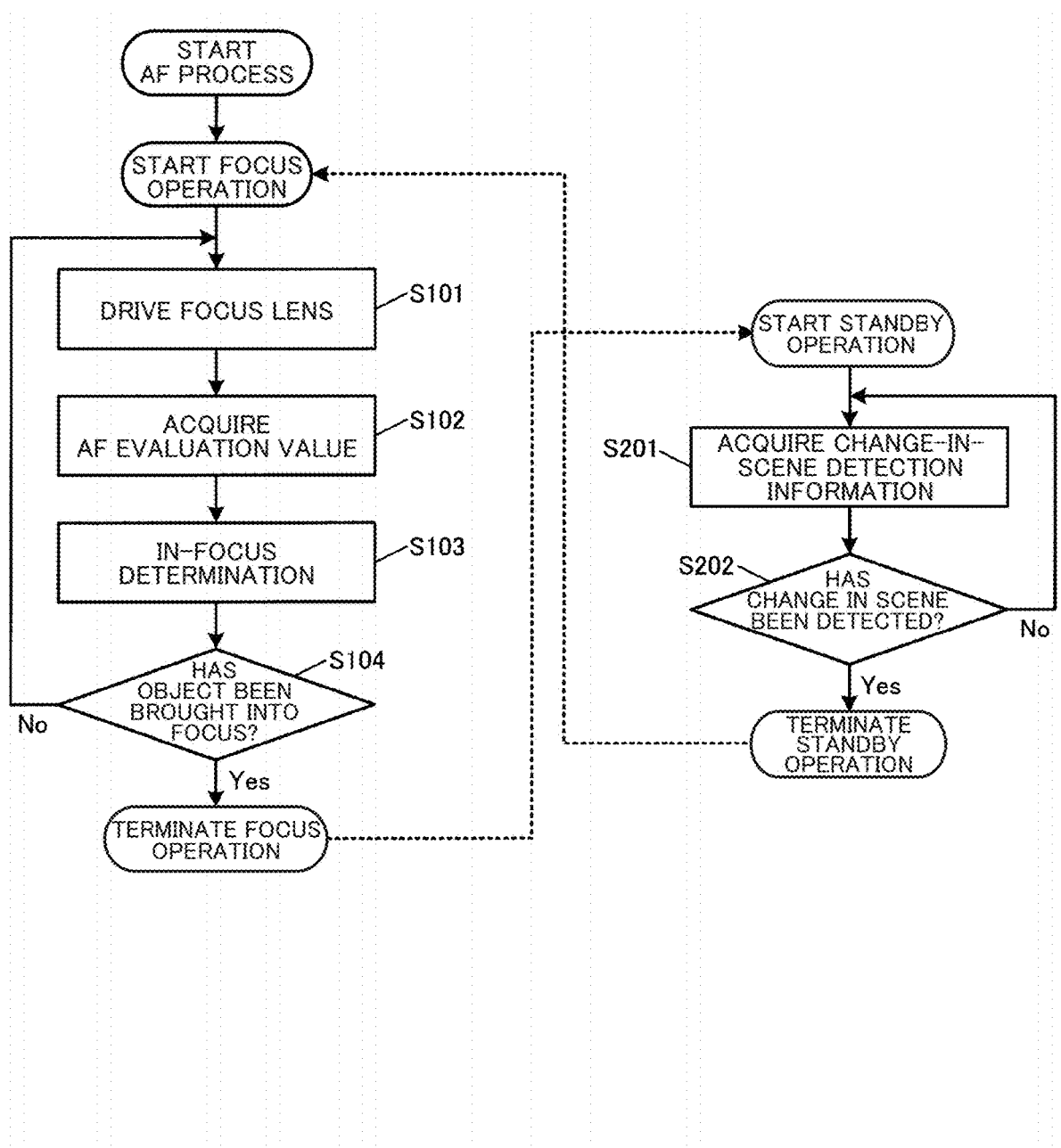
FIG. 4 is a flowchart illustrating a process according to one embodiment of the invention.

The details of the AF control section 345 are described below with reference to FIG. 4. When the AF control section 345 has started the AF process, the AF control section 345 starts a focus operation. The AF control section 345 drives the focus lens so that the focus operation is performed using a known peak detection method, wobbling peak direction determination method, and the like (S101), and acquires the AF evaluation value output from the AF evaluation value calculation section 344 (S102). The AF control section 345 performs a known in-focus determination process and the like to determine whether or not the object has been brought into focus (S103). When the object has not been brought into focus, the AF control section 345 repeats the steps S101 to S103. When the object has been brought into focus, the AF control section 345 terminates the focus operation (S104).

The AF control section 345 starts a standby operation after terminating the focus operation. Specifically, the AF control section 345 acquires the change-in-scene detection information output from the detection processing section 342 (S201). When a change in scene has not been detected, the AF control section 345 repeats the step S201. When a change in scene has been detected, the AF control section 345 terminates the standby operation (S202). When a change in scene continuously occurs for a long time, the AF control section 345 may terminate the standby operation after completion of the change in scene (not illustrated in the drawings), for example. The AF control section 345 resumes the focus operation after terminating the standby operation. Note that the AF control section 345 fixes the position of the focus lens to a position when the AF control section 345 terminated the focus operation (i.e., does not drive the focus lens) during the standby operation, for example.

The reason why the AF control section 345 performs the above control process is described below with reference to FIG. 5B. FIG. 5B is a view illustrating a typical image that is acquired by the endoscope system while the user performs treatment. The user performs treatment (e.g., excision of a lesion or suture) on a lesion that is situated around the center of the image using a treatment tool (e.g., electrosurgical knife or forceps) (see above). Therefore, a change in image becomes a maximum around the center of the image during treatment. Since the field of view does not change during treatment, and treatment is rarely performed in the peripheral area of the image, a change in image is relatively small in the peripheral area of the image.

In the first embodiment, an area that includes the peripheral area of the image is set to be the change-in-scene detection area (see FIG. 5A), a change in scene is detected using information acquired from the change-in-scene detection area, and the start (resumption) of the focus operation is controlled based on the detection result. The above control process makes it possible to stop (suspend) the focus operation (unnecessary focus operation) while the user performs treatment (while a change in scene does not occur), and resume the focus operation only when a change in scene has occurred, and the focus operation is required.

The change-in-scene detection method that is implemented by the detection processing section 342 is described below. The detection processing section 342 calculates the average brightness b_Y[i][n] of a plurality of blocks b[i] set to be the change-in-scene detection area from the current image, and stores the average brightness b_Y[i][n] in a memory (not illustrated in the drawings), for example. Note that i is the block number linked to each block. In the first embodiment, the number of blocks is nine, and i is a value from 0 to 8. n is the image acquisition timing.

The detection processing section 342 than calculates a change-in-scene detection evaluation value V using the following expression (1), for example. Note that b_Y[i][n−x] is the average brightness of each block calculated from the image acquired prior to the current image by x frames. x is an arbitrary number.

$$V = \sum_i \text{abs}(b\_Y[i][n] - b\_Y[i][n-x]) \quad (1)$$

Specifically, the evaluation value V is calculated by calculating the sum of the absolute values of the differences between the average brightness of each evaluation block calculated from the current image and the average brightness of each evaluation block calculated from the image acquired prior to the current image (see the expression (1)). Therefore, the evaluation value V increases as the difference between the current image and the image acquired prior to the current image by x frames increases.

The detection processing section 342 determines whether or not a change in scene has occurred using the calculated evaluation value V. For example, the detection processing section 342 determines that a change in scene has occurred when the evaluation value V has exceeded a given threshold value. The detection processing section 342 may determine that a change in scene has occurred when an arbitrary number of images for which the evaluation value V exceeds the given threshold value have been input successively, for example. Alternatively, the detection processing section 342 may determine that a change in scene has stopped when an arbitrary number of images for which the evaluation value V is equal to or smaller than the given threshold value have been input successively after a change in scene has occurred, for example. The detection processing section 342 outputs the determination result to the AF control section 345 as the change-in-scene detection information.

Although an example in which the average brightness is used as the feature quantity used to detect a change in scene has been described above, the configuration is not limited thereto. An arbitrary feature quantity from which a change in image can be detected (e.g., average color information about the evaluation blocks, or the AF evaluation value calculated from the evaluation blocks) may be used.

As described above, a change in image becomes a maximum around the center of the image during a period in which the user of the endoscope system performs treatment. Therefore, an area of the image other than the center may be set to be the change-in-scene detection area (see FIG. 6A), and a change in scene may be detected by performing a determination process similar to that described above.

The detection processing section 342 may detect a change in scene using the motion vector of each evaluation block. In this case, the detection processing section 342 calculates the motion vector of each evaluation block using a known technique. The detection processing section 342 then detects whether or not a change in scene has occurred using the motion vector calculation result for each evaluation block. FIG. 6B illustrates the motion vector of each evaluation block when the user has changed the position of the observation target object by moving the rigid scope 100 in the leftward direction, for example. FIG. 6C illustrates the motion vector of each evaluation block when the user has moved the rigid scope 100 closer to the object, for example. FIG. 6D illustrates the motion vector of each evaluation block when the user has moved the rigid scope 100 away from the object, for example. Therefore, the detection processing section 342 determines that a change in scene has occurred when the motion vector of each evaluation block has been calculated as illustrated in FIGS. 6B to 6D. The detection processing section 342 may determine that a change in scene has occurred when an arbitrary number of images that are considered to be a change in scene have been input successively, for example. Alternatively, the detection processing section 342 may determine that a change in scene has stopped when an arbitrary number of images that are not considered to be a change in scene have been input successively after a change in scene has occurred, for example. The above process makes it possible to accurately detect a change in scene independently of a local motion of the object, the treatment tool, or the like.

The endoscope system according to the first embodiment can thus suppress or reduce the occurrence of defocus or the like due to an unintentional change in focus position or erroneous AF control during a period in which the user performs treatment, and implement an AF control function that is convenient to the user.

Figure 6A:
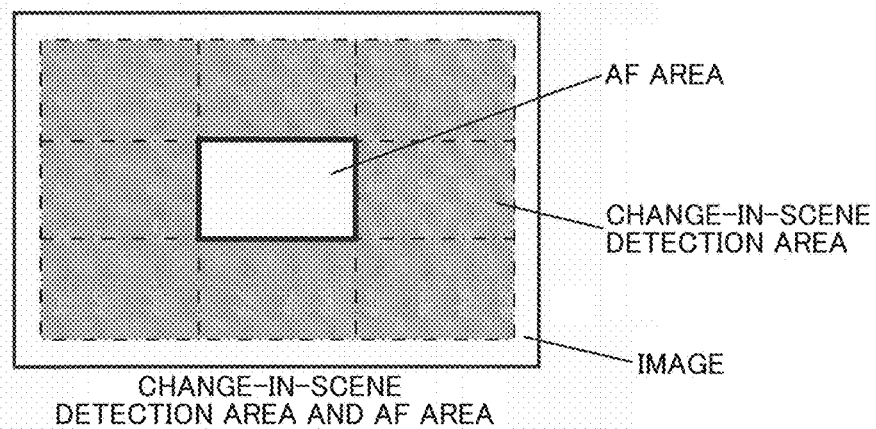
FIGS. 6A to 6D illustrate an example of a motion vector in each block included in a second area.
Figure 6B:
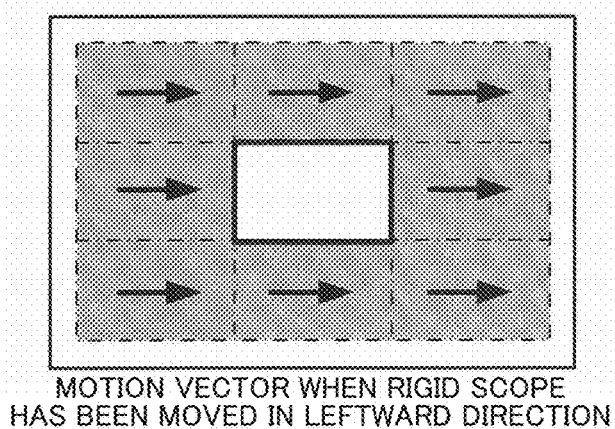
Figure 6C:
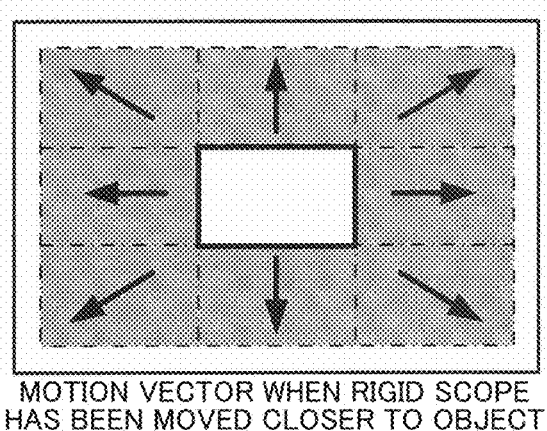
Figure 6D:
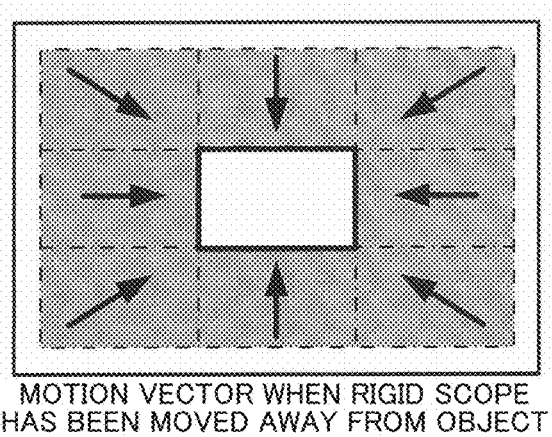

In the first embodiment, the second area (change-in-scene detection area) may be an area of the captured image that includes at least the peripheral area (see FIGS. 5A and 6A).

In the example illustrated in FIG. 5A, the second area is an area of the captured image that includes the center area and the peripheral area. In the example illustrated in FIG. 6A, the second area is an area of the captured image that includes the peripheral area, and does not include the center area. Note that the term "peripheral area" used herein refers to an area of the captured image that is situated away from the center of the image as compared with the center area. Various modifications may be made as to the setting of the boundary between the peripheral area and the center area. For example, since the center area is an area in which the treatment target object (i.e., the main object to which the user pays much attention) is captured (see FIG. 5B), the boundary between the peripheral area and the center area may be set from the viewpoint of ease of treatment (i.e., the ratio of the main object with respect to the entire image). In this case, each user may input the desired value, or a typical value stored in advance may be used.

Since it is considered that an object that differs from the treatment target (i.e., an object other than the main object) is captured in the peripheral area of the captured image, a change in object is small in the peripheral area even when the user performs treatment. Therefore, when an area that includes the peripheral area is used as the second area, a change in scene is not detected (i.e., the focus operation is not performed) even when the user performs treatment.

Note that the output image from the image sensor may only partially include the object image depending on the size of the image circle (as described layer in connection with the second embodiment). In such a case, since a change in image does not occur in an area of the output image other than the object-captured area that includes the object image, it is useless for the change-in-scene detection process to set the second area to include an area of the output image other than the object-captured area that includes the object image. Therefore, the term "captured image" used herein in a narrow sense may refer to an object-captured image that includes the object image.

The second area may be an area of the captured image that differs from the first area (AF area) (see FIG. 6A).

The first area is an area on which the AF process is performed, and it is considered that the main object is captured in the first area (see above). Therefore, a change in image occurs to a large extent in the first area during treatment. It is preferable that a change in image occur to only a small extent in the second area during treatment in order to prevent a situation in which the focus operation is unnecessarily performed during treatment. Specifically, the change-in-scene detection accuracy can be improved by setting an area that differs from the first area (in which a change in image occurs to a large extent) to be the second area.

Figure 7A:
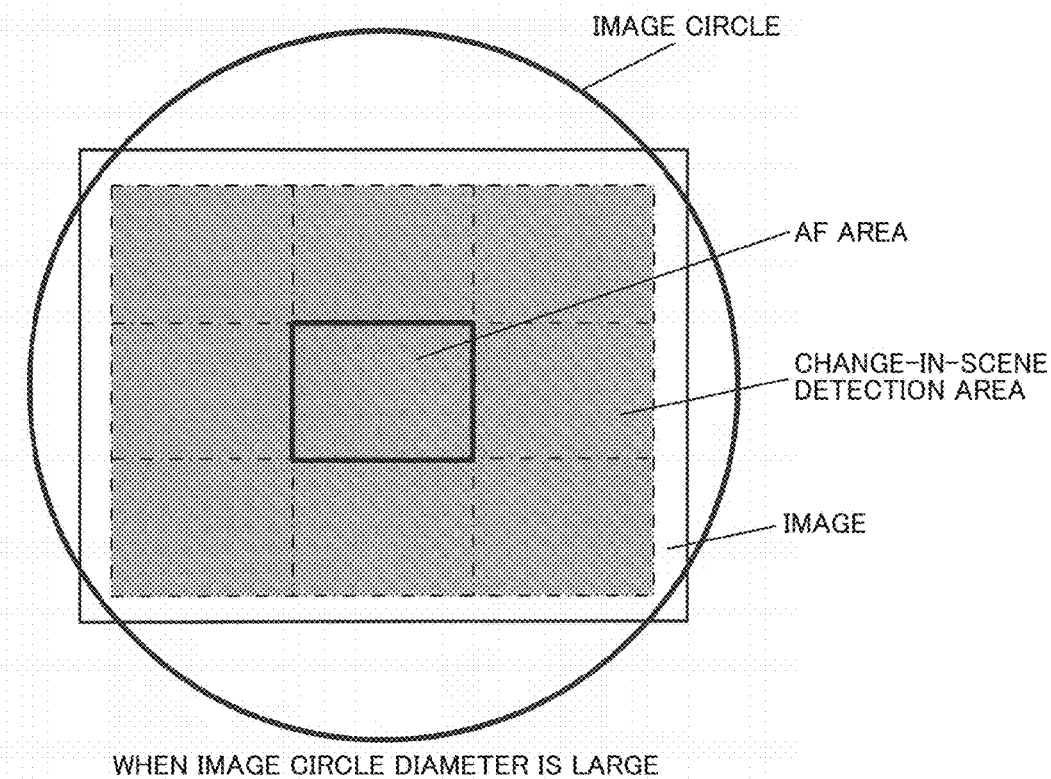
FIGS. 7A and 7B illustrate the relationship between an output image and an image circle.
Figure 7B:
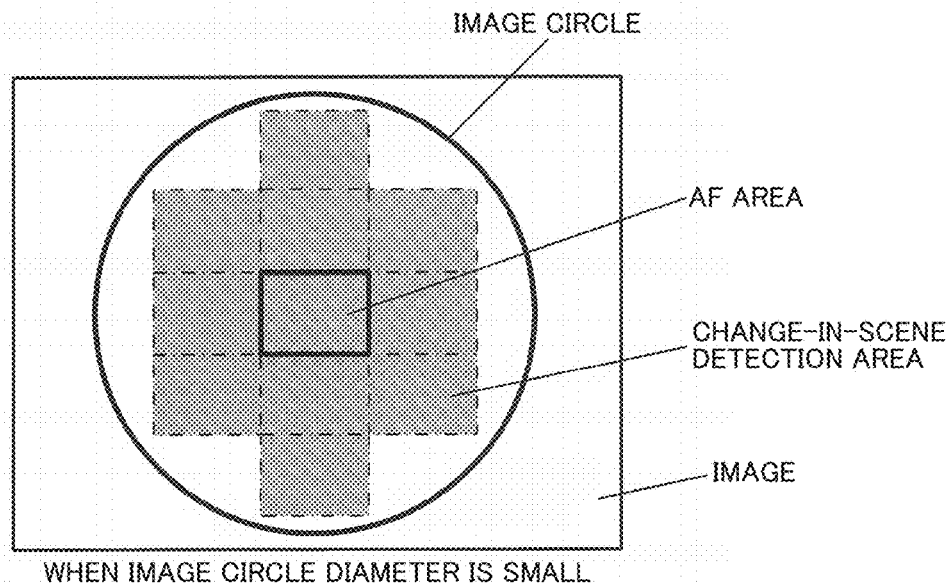

Note that an area of the captured image that differs from the first area need not necessarily be the entire area of the captured image other than the first area. As illustrated in FIGS. 6A, 7A, and 7B, the image (object-captured image) may include an area other than the first area and the second area. The expression "the first area and the second area differ from each other" may be interpreted to mean that the first area and the second area do not coincide with each other. This means that the first area and the second area may overlap each other, differing from the examples illustrated in FIG. 6A and the like. For example, the first area and the second area overlap each other when the second area includes the first area (see FIG. 5A).

The change-in-scene detection section 346 may stop the process that detects whether or not a change in scene has occurred (change-in-scene detection process) when the focus control process is performed by the focus control section 347. Note that the focus control process corresponds to the process that controls the focus operation (i.e., the steps S101 to S104 in the flowchart illustrated in FIG. 4), and the process that detects whether or not a change in scene has occurred is performed during the steps 201 and S202. Specifically, the change-in-scene detection section 346 stops the process that detects whether or not a change in scene has occurred when the focus operation is performed by the focus control section 347.

According to this configuration, since it is unnecessary to perform the change-in-scene detection process during the focus operation, it is possible to reduce the processing load. After the object has been brought into focus as a result of performing the focus operation, it is unlikely that the object becomes out of focus as long as a change in the relative positional relationship between the object and the imaging section 200 and the like do not occur. In the first embodiment, the focus operation is terminated after the object has been brought into focus, and the standby operation is performed (see FIG. 4). The change-in-scene detection process according to the first embodiment corresponds to a process that determines whether or not it is necessary to perform the focus operation again (i.e., it is impossible to bring the object into focus using the results of the previous focus operation). Specifically, since the change-in-scene detection process is typically used as a trigger for resuming (performing) the focus operation, it is likely that it is unnecessary to perform the change-in-scene detection process when the focus operation is performed, and it is possible to efficiently reduce the processing load by stopping the change-in-scene detection process. When capturing a video (moving image), the AF process in a narrow sense refers to a full-time AF process, and the change-in-scene detection process is a trigger for "resuming" the focus operation that has been stopped. When capturing a still image, the AF process in a narrow sense refers to a single AF process, and the change-in-scene detection process is a trigger for "performing" the second (or the third or subsequent) focus operation.

The change-in-scene detection section 346 may determine that a change in scene has not occurred when it has been determined that the motion of the object has not been detected in the peripheral area of the captured image even if it has been determined that the motion of the object has been detected in the center area of the captured image.

The motion detection process may be implemented using the motion vector (see FIGS. 6B to 6D), for example. As described above, the motion of the object is large in the center area (e.g., an area corresponding to the AF area illustrated in FIG. 6A) of the image, and is small in the peripheral area (change-in-scene detection area illustrated in FIG. 6A) of the image during treatment. When using a known method, it is determined that a change in scene has occurred when the motion of the object is large in the center area of the image. According to the above configuration, however, it is possible to reduce the possibility that it is erroneously determined that a change in scene has occurred during treatment. Note that the expression "the motion of the object has not been detected" does not necessarily mean that the motion of the object is 0. Specifically, the object captured in the peripheral area may make a small motion when treatment is performed on the object captured in the center area, or the imaging section 200 may make a motion due to shake or the like, or the object may make a motion due to pulsation, peristalsis, or the like depending on the position of the object. Since such a motion is small, it is unnecessary to perform the focus operation (i.e., it should not be determined that a change in scene has been detected). For example, a motion threshold value that can be used to distinguish a large motion (that corresponds to a situation in which the focus operation is necessary (see FIGS. 6B to 6D)) and a small motion may be set, it may be determined that the motion of the object has not been detected when the motion amount is smaller than the motion threshold value, and it may be determined that the motion of the object has been detected when the motion amount is equal to or larger than the motion threshold value.

The expression "even if it has been determined that the motion of the object has been detected in the center area of the captured image" does not necessarily mean that the motion of the object in the center area of the captured image is detected. Specifically, the motion of the object in the center area of the image may be detected, and the detection result may not be used, or the motion of the object in the center area of the image may not be detected. For example, when using the change-in-scene detection area illustrated in FIG. 6A, the motion of the object in the center area of the image is not detected.

The second area may be a set of a plurality of blocks, and the change-in-scene detection section 346 may detect whether or not a change in scene has occurred based on a comparison process that compares the motion pattern of the object in the plurality of blocks with a given reference motion pattern.

Note that the motion pattern of the object in the plurality of blocks refers to a set of motions (motion vectors in a narrow sense) calculated corresponding to the respective blocks. For example, when the second area includes eight blocks (see FIG. 6A), the motion pattern is a set of eight motion vectors. It is possible to acquire information that represents that a motion in a given direction has been detected from all of the blocks, or information that represents that radial motions have been detected with respect to the center of the image (see FIGS. 6B to 6D), by utilizing the motion pattern.

The term "reference motion pattern" used herein refers to information that is stored in advance and represents a typical motion pattern that occurs when the relative relationship between the imaging section 200 and the object changes (when the imaging section 200 is moved in a narrow sense). For example, a motion pattern in a given direction (see FIG. 6B) is detected when the imaging section 200 has moved in a plane that intersects (perpendicularly intersects in a narrow sense) the optical axis direction. A radial motion pattern is detected when the imaging section 200 has moved in the optical axis direction. These motion patterns may be used as the reference motion pattern.

When such a typical movement of the imaging section 200 and the reference motion pattern that corresponds to the typical movement of the imaging section 200 are stored in advance, it is possible to determine that the imaging section 200 has made a motion that corresponds to the reference motion pattern when a motion pattern similar to the reference motion pattern has been detected. It is possible to detect whether or not a change in scene has occurred from the motion pattern through the comparison process that compares the motion pattern with the reference motion pattern by storing the reference motion pattern that corresponds to a situation in which the imaging section 200 has moved to a large extent, and it is necessary to resume the focus operation (see FIGS. 6B to 6D) (i.e., a situation in which it should be determined that a change in scene has occurred).

Note that part or most of the processes performed by the endoscope apparatus and the like according to the first embodiment may be implemented by a program. In this case, the endoscope apparatus and the like according to the first embodiment are implemented by causing a processor (e.g., CPU) to execute a program. More specifically, a program stored in an information storage device is read, and executed by a processor (e.g., CPU). The information storage device (computer-readable device) stores a program, data, and the like. The function of the information storage device may be implemented by an optical disk (e.g., DVD or CD), a hard disk drive (HDD), a memory (e.g., memory card or ROM), or the like. The processor (e.g., CPU) performs various processes according to the first embodiment based on the program (data) stored in the information storage device. Specifically, a program that causes a computer (i.e., a device that includes an operation section, a processing section, a storage section, and an output section) to function as each section according to the first embodiment (i.e., a program that causes a computer to execute the process implemented by each section according to the first embodiment) is stored in the information storage device.

The endoscope apparatus according to the embodiments of the invention may include a memory that stores information (e.g., a program and various types of data), and a processor that operates based on the information stored in the memory. The processor performs a focus control process that controls the position of a focus lens to an in-focus position based on an in-focus evaluation value, the focus lens being included in an optical system that forms an image included in a captured image that is acquired by an imaging section, and the in-focus evaluation value being calculated from a first area within the captured image, and a change-in-scene detection process that detects whether or not a change in scene has occurred from a second area within the captured image that includes an area that differs from at least the first area, wherein the processor is set to a standby state in which the processor stops the focus control process when the focus control process has controlled the position of the focus lens to the in-focus position, and resumes the focus control process when the change in scene has been detected by the change-in-scene detection process when the processor is set to the standby state.

The processor may implement the function of each section by independent (individual hardware), or may implement the function of each section by integrated hardware, for example. The processor may be a central processing unit (CPU), for example. Note that the processor is not limited to a CPU. Various other processors such as a graphics processing unit (GPU) or a digital signal processor (DSP) may also be used. The processor may be a hardware circuit that includes an application specific integrated circuit (ASIC). The memory may be a semiconductor memory (e.g., SRAM or DRAM), a register, a magnetic storage device (e.g., hard disk drive), or an optical storage device (e.g., optical disk device). For example, the memory stores a computer-readable instruction, and each section of the endoscope apparatus is implemented by causing the processor to execute the instruction. The instruction may be an instruction included in an instruction set that is included in a program, or may be an instruction that causes a hardware circuit included in the processor to operate.

The operation according to the embodiments of the invention is implemented as described below, for example. The processor acquires the captured image, and stores the captured image in the memory. The memory stores information that represents (specifies) the first area within the captured image, and information that represents (specifies) the second area within the captured image, and the processor reads the captured image and the information that represents (specifies) the first area from the memory, calculates the in-focus evaluation value from the first area within the captured image, and performs the focus control process. The processor also reads the captured image and the information that represents (specifies) the second area from the memory, and performs the change-in-scene detection process that detects whether or not a change in scene has occurred from the second area within the captured image.

Each section of the endoscope apparatus according to the embodiments of the invention is implemented as a module of a program that operates on the processor. For example, the focus control section is implemented as a focus control module that controls the position of a focus lens to an in-focus position based on an in-focus evaluation value, the focus lens being included in an optical system that forms an image included in a captured image that is acquired by an imaging section, and the in-focus evaluation value being calculated from a first area within the captured image. The change-in-scene detection section is implemented as a change-in-scene detection module that detects whether or not a change in scene has occurred from a second area within the captured image that includes an area that differs from at least the first area.

The endoscope apparatus and the like according to the first embodiment may include a processor and a memory. The processor may be a central processing unit (CPU), for example. Note that the processor is not limited to a CPU. Various other processors such as a graphics processing unit (GPU) or a digital signal processor (DSP) may also be used. The processor may be a hardware circuit that includes an ASIC. The memory stores a computer-readable instruction. Each section of the endoscope apparatus and the like according to the first embodiment is implemented by causing the processor to execute the instruction. The memory may be a semiconductor memory (e.g., SRAM or DRAM), a register, a hard disk, or the like. The instruction may be an instruction included in an instruction set that is included in a program, or may be an instruction that causes a hardware circuit included in the processor to operate.

3. Second Embodiment

An endoscope system according to the second embodiment is described below. The endoscope system according to the second embodiment is configured in the same manner as described above in connection with the first embodiment.

The endoscope system according to the second embodiment is characterized in that the image circle diameter of the object image formed on the image sensor 260 changes depending on the type of the rigid scope 100 connected to the imaging section 200, or the optical magnification of the objective lens system 270 determined by the position of the zoom lens 240, for example. FIG. 7A is a view illustrating an image acquired by the image sensor 260 when the image circle diameter is large, and FIG. 7B is a view illustrating an image acquired by the image sensor 260 when the image circle diameter is small. Since the object image is formed inside the image circle, a change in image cannot be detected when the change-in-scene detection area is set to the outside of the image circle. Therefore, the endoscope system according to the second embodiment must adjust the change-in-scene detection area corresponding to the image circle diameter. Since the size of the object within the image changes along with a change in image circle diameter, it is desirable to adjust the size of the AF area corresponding to the image circle diameter.

The endoscope system according to the second embodiment is designed so that the rigid scope 100 includes a memory (not illustrated in the drawings) that stores rigid scope type information, and the control section 350 acquires the rigid scope type information from the memory when the rigid scope 100 has been connected to the imaging section 200. The endoscope system according to the second embodiment is designed so that the user inputs the rigid scope type information to the external I/F section 500, for example. In this case, the external I/F section 500 outputs the rigid scope type information input by the user to the control section 350. The endoscope system according to the second embodiment is designed so that zoom lens position information is output to the control section 350 when the user has adjusted the position of the zoom lens 240 using the zoom button 210, for example.

The control section 350 outputs the rigid scope type information and the zoom lens position information to the change-in-scene detection area setting section 341 and the AF area setting section 343. The change-in-scene detection area setting section 341 calculates the image circle diameter from the rigid scope type information and the zoom lens position information, and adjusts the change-in-scene detection area corresponding to the image circle diameter. Specifically, the change-in-scene detection area setting section 341 changes the size, the number, the position, and the arrangement (arrangement method) of the evaluation blocks that are set to be the change-in-scene detection area (see FIGS. 7A and 7B). The AF area setting section 343 calculates the image circle diameter from the rigid scope type information and the zoom lens position information, and adjusts the AF area corresponding to the image circle diameter. Specifically, the AF area setting section 343 changes the size and the position of the AF area (see FIGS. 7A and 7B).

The endoscope system according to the second embodiment can thus optimize the change-in-scene detection area and the AF area even when the image circle diameter of the object image formed on the image sensor 260 changes depending on the type of the rigid scope 100 or the position of the zoom lens 240.

According to the second embodiment, the second area is a set of a plurality of blocks, and at least one of the number, the size, and the arrangement of the blocks is changed based on the size of the image circle of the object image formed on the image sensor 260 by the optical system.

Note that the block corresponds to the evaluation block (see above). In the example illustrated in FIG. 5A and the like, the second area is a set of nine blocks (3×3 blocks). When the number, the size, and the arrangement of the blocks are changed as illustrated in FIGS. 7A and 7B, the number of blocks is changed from 9 to 11, the size of one block is decreased, and blocks are added on the upper side and the lower side of the 3×3 rectangular blocks.

This makes it possible to appropriately set the second area. The object image is formed only inside the image circle within the output image output from the image sensor 260. Since the image circle diameter changes corresponding to the type of the rigid scope 100, the zoom magnification of the optical system, and the like, the area (object-captured image) in which the object image is formed also changes. The second embodiment is designed on the assumption that the main object that is the treatment target and changes to a large extent is captured within part (center area in a narrow sense) of the image, and the object captured within the remaining area (peripheral area in a narrow sense) changes to only a small extent. The term "image" used in connection with the second embodiment may refer to a range in which the object image is formed, and the object-captured image may be used as the image.

Since the size of the object-captured image basically increases as the size of the image circle increases, the size of each block may be increased when forming the second area using an identical number of blocks. The number of blocks may be increased when it is desired to maintain the size of each block when the size of the object-captured image has increased.

The arrangement of the blocks included in the second area may be changed based on shape information about the object-captured image including the object image that is determined by the image circle.

The object-captured image has a rectangular shape when the image circle is sufficiently large with respect to the image sensor 260, has a circular shape when the image circle lies within the image sensor 260 (see FIG. 7B), and has an intermediate shape between a rectangle and a circle when the image circle has an intermediate size (see FIG. 7A). When the object-captured image has a shape close to a rectangle, it is possible to cover a wide range by setting the second area to have a rectangular shape (see FIG. 7A). When the object-captured image has a circular shape, the peripheral area of the object-captured image cannot be covered using a rectangular second area, and it is impossible to appropriately detect a change in scene. In this case, it is desirable to change the shape of the second area. When a set of blocks having a given shape is set to be the second area, the arrangement of the blocks is changed as illustrated in FIG. 7B.

At least one of the size and the position of the first area may be changed based on the size of the image circle of the object image formed on the image sensor 260 by the optical system.

As described above, the position and the size of the main object within the image change due to a change in image circle. The first area is the in-focus evaluation value calculation target area, and corresponds to an area in which the main object is captured. Therefore, it is possible to perform an appropriate focus control process by changing the size and the like of the first area based on the image circle diameter in addition to the second area.

4. Third Embodiment

When a bright spot due to the reflection of the illumination light is included within the image, the bright spot has a very large brightness value. When a treatment tool (e.g., forceps) is captured within the image, the area in which the treatment tool is captured differs in pixel value and brightness value to a large extent from the tissue area since the color of the treatment tool differs to a large extent from the color of tissue. A very small brightness value is acquired in a dark area in which the amount of light is insufficient, and the dark area significantly differs in signal value from a normal tissue area.

The change-in-scene detection accuracy may decrease if the information about such a specific point (area) is used. In the third embodiment, a bright spot or the like is excluded from the second area instead of using the information about the entire second area for the change-in-scene detection process. This makes it possible to accurately detect whether or not a change in scene has occurred.

Figure 8:
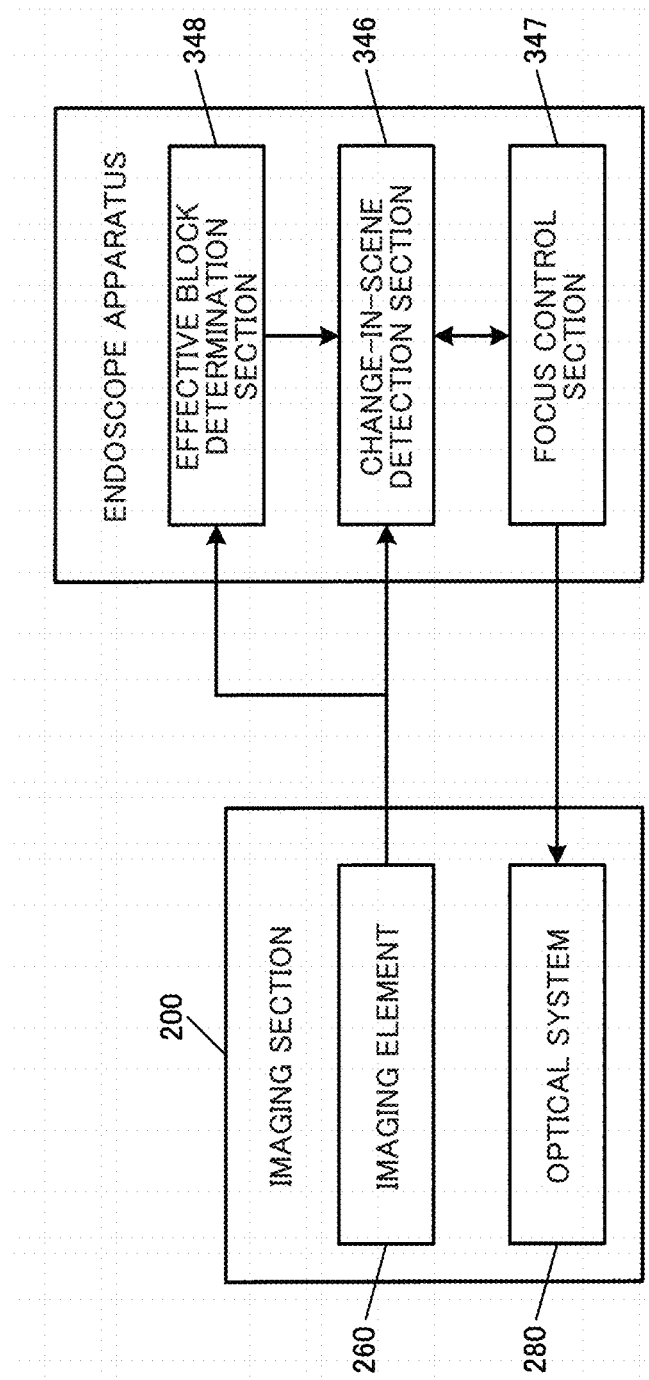
FIG. 8 illustrates another configuration example of an endoscope apparatus according to one embodiment of the invention.

More specifically, the endoscope apparatus may include an effective block determination section 348 (see FIG. 8). When the second area includes a plurality of blocks (evaluation blocks), the effective block determination section 348 determines whether each block is an effective block that does not include a bright spot or the like or an ineffective block that includes a bright spot or the like. The change-in-scene detection section 346 detects whether or not a change in scene has occurred using only the effective blocks among the blocks included in the second area.

Figure 9:
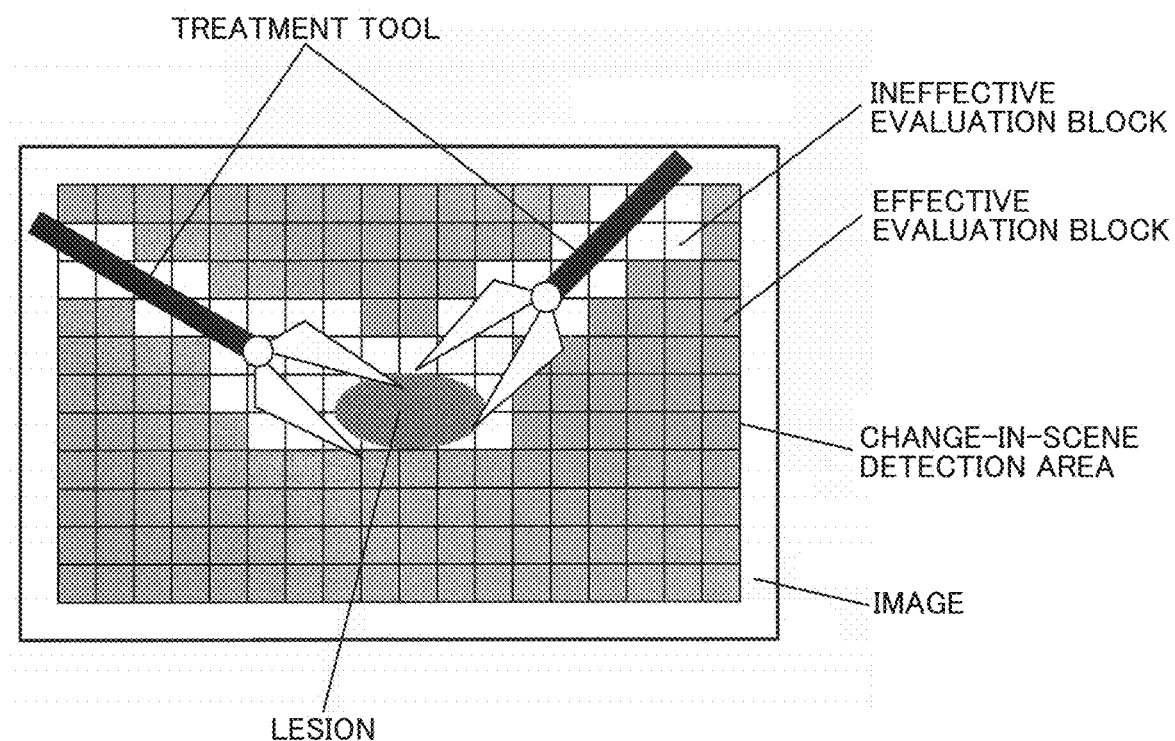
FIG. 9 illustrate the relationship between a treatment tool and an effective block/ineffective block.

Note that the size of one block may be changed in various ways. For example, one pixel may be used as one block. However, when the size of the block is decreased, and the number of blocks included within the image is increased, the processing load of the process that determines whether or not each block is the effective block increases. On the other hand, when the size of the block is increased, and the number of blocks included within the image is decreased to a large extent (see FIG. 5A), most (all in a narrow sense) of the blocks may be determined to be the ineffective block even when the area of a bright spot or a treatment tool within the image is moderate, and it may be difficult to appropriately detect whether or not a change in scene has occurred. Therefore, it is preferable to set the size of the block (the number of blocks) to an appropriate value taking account of the balance between the processing load and the effective block determination process. For example, the size and the like illustrated in FIG. 9 may be used.

The effective block determination section 348 determines whether or not each evaluation block is the effective block using a feature quantity calculated corresponding to each evaluation block. For example, the effective block determination section 348 may determine whether or not the maximum Y signal value (brightness value) among the Y signal values (brightness values) of all of the pixels included in each evaluation block is equal to or larger than given threshold value. The effective block determination section 348 may determine that the evaluation block is not the effective block when the maximum brightness value is equal to or larger than the given threshold value on the assumption that a bright spot is included in the evaluation block, and set an effective block determination flag of the evaluation block to "0". The effective block determination section 348 may determine that the evaluation block is the effective block when the maximum brightness value is smaller than the given threshold value on the assumption that a bright spot is not included in the evaluation block, and set the effective block determination flag of the evaluation block to "1".

For example, the effective block determination section 348 determines whether or not the average value of the Y signal values (brightness values) of all of the pixels included in each evaluation block is equal to or smaller than a given threshold value. The effective block determination section 348 determines that the evaluation block is not the effective block when the average value is equal to or smaller than the given threshold value on the assumption that the evaluation block is situated in a very dark area within the image, and sets the effective block determination flag of the evaluation block to "0". The effective block determination section 348 determines that the evaluation block is the effective block when the average value is larger than the given threshold value on the assumption that the evaluation block is situated in a bright area within the image, and sets the effective block determination flag of the evaluation block to "1".

For example, the effective block determination section 348 determines whether or not both the average Cb signal value and the average Cr signal value of each evaluation block are equal to or smaller than a given threshold value. The effective block determination section 348 determines that the evaluation block is not the effective block when both the average Cb signal value and the average Cr signal value are equal to or smaller than the given threshold value on the assumption that the evaluation block is situated in a forceps area within the image, and sets the effective block determination flag of the evaluation block to "0". Specifically, since the color of forceps is normally black or silver, both the Cb signal and the Cr signal have a value close to 0 in the forceps area within the image. The effective block determination section 348 determines that the evaluation block is the effective block when both the average Cb signal value and the average Cr signal value are larger than the given threshold value, or either of the average Cb signal value and the average Cr signal value is larger than the given threshold value, on the assumption that the evaluation block is not situated in a forceps area within the image, and sets the effective block determination flag of the evaluation block to "1".

The effective block determination section 348 performs one of the above determination processes, or performs a plurality of determination processes among the above determination processes in an arbitrary combination, and outputs the effective block determination flag of each evaluation block to the change-in-scene detection section 346 (detection processing section 342). When the effective block determination section 348 performs a plurality of determination processes, the effective block determination section 348 may set the effective block determination flag to "1" when the evaluation block has been determined to be the effective block by all of the plurality of determination processes. The effective block determination section 348 may set the effective block determination flag to "0" when the evaluation block has been determined to be the ineffective block by at least one of the plurality of determination processes.

The effective block determination section 348 may optionally calculate an arbitrary feature quantity other than the above feature quantities, and perform an arbitrary determination process corresponding to the calculated feature quantity to determine whether or not each evaluation block is the effective block.

According to the third embodiment, the endoscope apparatus further includes the effective block determination section 348 that determines whether or not each of a plurality of blocks is effective when the second area is a set of the plurality of blocks, and the change-in-scene detection section 346 detects whether or not a change in scene has occurred from a block among the plurality of blocks included in the second area that has been determined to be effective by the effective block determination section 348.

According to this configuration, since the information about an area (e.g., bright spot, dark area, or treatment tool area) in which a specific signal value is output as compared with an area in which tissue is normally captured can be excluded from the target of the change-in-scene detection process, it is possible to accurately detect whether or not a change in scene has occurred.

Note that the accuracy of the in-focus evaluation value calculation process also decreases due to the information about a bright spot, a dark area, or a treatment tool area. Therefore, the effective block determination section 348 may output the effective block determination results to the focus control section 347 (AF evaluation value calculation section 344), and the focus control section 347 may calculate the in-focus evaluation value using information about a block among the blocks included in the first area that has been determined to be effective. This makes it possible to accurately calculate the in-focus evaluation value.

However, when the effect of the information about a bright spot or the like on the calculation of the in-focus evaluation value is also taken into consideration, it may be difficult to sufficiently eliminate the effect by merely detecting a block that includes a bright spot or forceps from the captured image at each timing, and performing the focus control process while excluding the detected block from the first area. This is because the position of the exclusion target object within the image may change during the focus operation (e.g., when the position of a bright spot within the image has changed due to a small motion (movement) of tissue (object)). The focus operation that utilizes the in-focus evaluation value determines an appropriate position of the focus lens by comparing the in-focus evaluation values at each timing, and detecting a relative peak. Therefore, when the number and the arrangement of effective blocks within the image at a first timing differ from the number and the arrangement of effective blocks within the image at a second timing, the in-focus evaluation value calculation conditions differ between the two images, and it is difficult to appropriately compare two in-focus evaluation values.

Figure 10A:
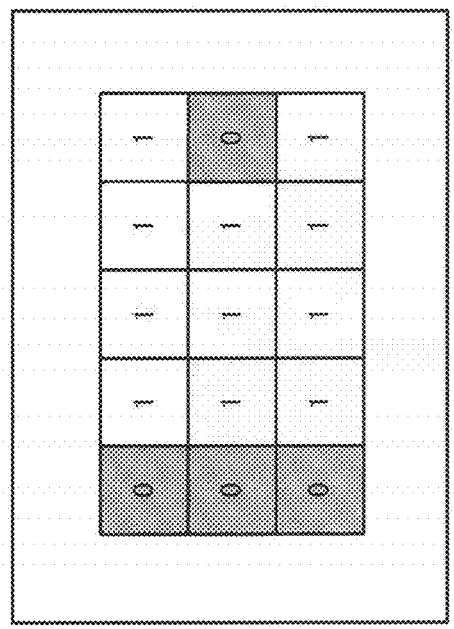
FIGS. 10A to 10C illustrate an example in which an effective block included in a first area is set based on determination results obtained using a plurality of images.
Figure 10B:
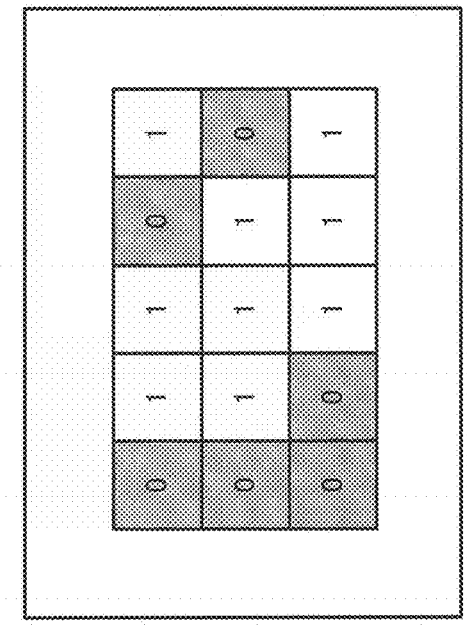
Figure 10C:
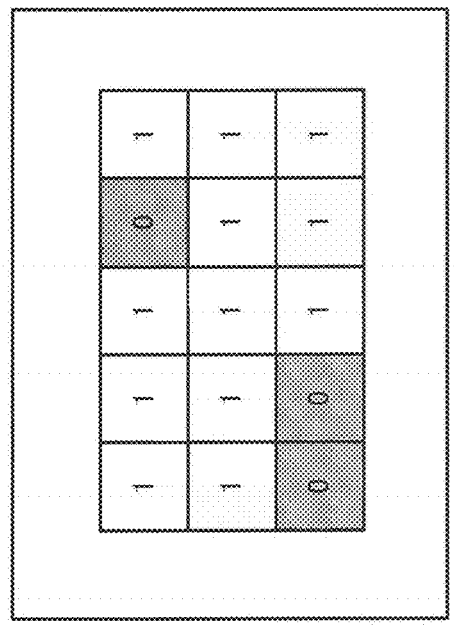

In order to deal with the above problem, the effective block included in the first area may be determined using the information about the effective block at a plurality of timings instead of using only the information about the effective block at one timing, for example. FIGS. 10A to 10C illustrate a specific example. For example, a first image and a second image are acquired during the focus operation. FIG. 10A illustrates the effective block determination results for the first image, and FIG. 10B illustrates the effective block determination results for the second image. In FIGS. 10A and 10B, the flag of the effective block is set to "1", and the flag of the ineffective block is set to "0". In this case, a set of the blocks that have been determined to be effective within both the first image and the second image is determined to be the effective blocks included in the first area (see FIG. 10). According to this configuration, since the in-focus evaluation value can be calculated from a plurality of images under the same conditions, it is possible to appropriately perform the in-focus evaluation value comparison process.

The first to third embodiments to which the invention is applied and the modifications thereof have been described above. Note that the invention is not limited to the first to third embodiments and the modifications thereof. Various modifications and variations may be made without departing from the scope of the invention. A plurality of elements described above in connection with the first to third embodiments and the modifications thereof may be appropriately combined to implement various configurations. For example, an arbitrary element may be omitted from the elements described above in connection with the first to third embodiments and the modifications thereof. Some of the elements described above in connection with different embodiments or modifications thereof may be appropriately combined. Any term cited with a different term having a broader meaning or the same meaning at least once in the specification and the drawings can be replaced by the different term in any place in the specification and the drawings. Specifically, various modifications and applications are possible without materially departing from the novel teachings and advantages of the invention.

What is claimed is:

1. An endoscope apparatus comprising:
a processor comprising hardware, the processor being configured to perform processes comprising:
a focus control process that controls a position of a focus lens to an in-focus position based on an in-focus evaluation value, the focus lens being included in an optical system that forms an image included in a captured image that is acquired by an imaging section, and the in-focus evaluation value being calculated from a first area within the captured image; and
a change-in-scene detection process that detects whether or not a change in scene has occurred from a second area within the captured image that includes an area that differs from at least the first area,
wherein the processor is set to a standby state in which the processor stops the focus control process when the focus control process has controlled the position of the focus lens to the in-focus position, and resumes the focus control process when the change in scene has been detected by the change-in-scene detection process when the processor is set to the standby state, wherein the first area is an area in the image corresponding to an area of tissue where a treatment is performed with a treatment tool,
wherein the second area is an area in the image corresponding to an area of tissue where the treatment is not performed with the treatment tool,
wherein the second area is an area of the captured image that includes at least a peripheral area,
wherein the second area comprises a plurality of blocks, and
wherein the processor, in the change-in-scene detection process, detects whether or not the change in scene has occurred based on a motion pattern of an object in the plurality of blocks.

2. The endoscope apparatus as defined in claim 1, wherein at least one of a number, a size, and an arrangement of the blocks is changed based on a size of an image circle of an object image that is formed by the optical system on an image sensor that is included in the imaging section.

3. The endoscope apparatus as defined in claim 2, wherein at least the arrangement of the blocks included in the second area is changed based on shape information about an object-captured image including the object image that is determined by the image circle.

4. The endoscope apparatus as defined in claim 1, wherein at least one of a size and a position of the first area is changed based on a size of an image circle of an object image that is formed by the optical system on an image sensor that is included in the imaging section.

5. The endoscope apparatus as defined in claim 1, wherein the processor stops the change-in-scene detection process when the focus control process is performed.

6. The endoscope apparatus as defined in claim 1, wherein the processor determines in the change-in-scene detection process that the change in scene has not occurred when it has been determined that motion has not been detected in a peripheral area of the captured image even if it has been determined that motion has been detected in a center area of the captured image.

7. The endoscope apparatus as defined in claim 1, wherein the processor determines, in the change-in-scene detection process, whether or not the change in scene has occurred based on a comparison process that compares the motion pattern of the object in the plurality of blocks with a reference motion pattern.

8. The endoscope apparatus as defined in claim 1, wherein the processor is configured to further perform an effective block determination process that determines whether or not each of the plurality of blocks of the second area is effective, and
wherein the processor determines, in the change-in-scene detection process, whether or not the change in scene has occurred from blocks among the plurality of blocks of the second area that have been determined to be effective by the effective block determination process.

9. A method for controlling an endoscope apparatus, the method comprising:

calculating an in-focus evaluation value from a first area within a captured image acquired by an imaging section;

performing a focus control process that controls a position of a focus lens to an in-focus position based on the in-focus evaluation value, the focus lens being included in an optical system included in the imaging section;

detecting whether or not a change in scene has occurred from a second area within the captured image that includes an area that differs from at least the first area; and resuming the focus control process when the change in scene has been detected in a standby state in which the focus control process is stopped after the focus control process has controlled the position of the focus lens to the in-focus position, wherein the first area is an area in the image corresponding to an area of tissue where a treatment is performed with a treatment tool, wherein the second area is an area in the image corresponding to an area of tissue where the treatment is not performed with the treatment tool, wherein the second area is an area of the captured image that includes at least a peripheral area, wherein the second area comprises a plurality of blocks, and wherein the detecting whether or not the change in scene has occurred is performed based on a motion pattern of an object in the plurality of blocks.

10. A computer-readable storage device with an executable program stored thereon, wherein the program instructs a microprocessor to perform processes comprising:

calculating an in-focus evaluation value from a first area within a captured image acquired by an imaging section;

performing a focus control process that controls a position of a focus lens to an in-focus position based on the in-focus evaluation value, the focus lens being included in an optical system included in the imaging section;

detecting whether or not a change in scene has occurred from a second area within the captured image that includes an area that differs from at least the first area; and resuming the focus control process when the change in scene has been detected in a standby state in which the focus control process is stopped after the focus control process has controlled the position of the focus lens to the in-focus position, wherein the first area is an area in the image corresponding to an area of tissue where a treatment is performed with a treatment tool, wherein the second area is an area in the image corresponding to an area of tissue where the treatment is not performed with the treatment tool, wherein the second area is an area of the captured image that includes at least a peripheral area, wherein the second area comprises a plurality of blocks, and wherein the detecting whether or not the change in scene has occurred is performed based on a motion pattern of an object in the plurality of blocks.

11. The endoscope apparatus as defined in claim 1, wherein the motion pattern of the object in the plurality of blocks comprises a motion vector for each of the plurality of blocks.

12. The endoscope apparatus as defined in claim 7, wherein the reference motion pattern includes a plurality of motion patterns corresponding to different movements of the imaging section relative to an object of the captured image.

13. The endoscope apparatus as defined in claim 7, wherein the reference motion pattern includes a plurality of motion patterns, the plurality of motion patterns comprising a motion pattern corresponding to movement of the imaging section relative to an object of the captured image in an optical axis direction and a motion pattern corresponding to movement of the imaging section relative to the object in a plane intersecting the optical axis direction.

14. The endoscope apparatus as defined in claim 8, wherein the effective block determination process determines that blocks including the treatment tool in the captured image are not effective.

* * * * *